(12) United States Patent
Ninomiya et al.

US011969436B2

(10) Patent No.: US 11,969,436 B2
(45) Date of Patent: Apr. 30, 2024

(54) METHOD FOR TREATING SKIN IRRITATION CAUSED BY PARABENS

(71) Applicant: Kao Corporation, Tokyo (JP)

(72) Inventors: Rie Ninomiya, Fujisawa (JP);
Takafumi Nishijima, Tochigi (JP);
Noriko Sato, Tochigi (JP)

(73) Assignee: Kao Corporation, Tokyo (JP)

( * ) Notice: Subject to any disclaimer, the term of this patent is extended or adjusted under 35 U.S.C. 154(b) by 349 days.

(21) Appl. No.: 16/768,180

(22) PCT Filed: Nov. 29, 2018

(86) PCT No.: PCT/JP2018/043990
§ 371 (c)(1),
(2) Date: May 29, 2020

(87) PCT Pub. No.: WO2019/107496
PCT Pub. Date: Jun. 6, 2019

(65) Prior Publication Data
US 2020/0289538 A1 Sep. 17, 2020

(30) Foreign Application Priority Data

Nov. 30, 2017 (JP) .................................. 2017-230473
May 22, 2018 (JP) .................................. 2018-097850

(51) Int. Cl.
*A61K 31/7028* (2006.01)
*A61K 31/26* (2006.01)
*A61K 36/31* (2006.01)
*A61P 17/04* (2006.01)
*A61Q 19/00* (2006.01)
*C12Q 1/44* (2006.01)
*G01N 33/50* (2006.01)

(52) U.S. Cl.
CPC .......... *A61K 31/7028* (2013.01); *A61K 31/26* (2013.01); *A61K 36/31* (2013.01); *A61P 17/04* (2018.01); *C12Q 1/44* (2013.01); *G01N 33/5023* (2013.01)

(58) Field of Classification Search
None
See application file for complete search history.

(56) References Cited

U.S. PATENT DOCUMENTS

| 8,927,007 | B2* | 1/2015 | Talalay | .................. | A61K 9/127 |
| | | | | | 424/94.61 |
| 2003/0091518 | A1 | 5/2003 | Pauly et al. | | |
| 2008/0254055 | A1* | 10/2008 | Oblong | .................... | A61K 8/67 |
| | | | | | 424/766 |
| 2011/0009486 | A1 | 1/2011 | Kepley et al. | | |
| 2011/0014137 | A1* | 1/2011 | Talalay | ..................... | A61P 1/04 |
| | | | | | 424/59 |
| 2011/0150774 | A1* | 6/2011 | Rivier | ................. | G01N 33/6893 |
| | | | | | 435/7.1 |
| 2012/0258060 | A1* | 10/2012 | Talalay | .................. | A61P 17/00 |
| | | | | | 424/59 |
| 2013/0164365 | A1* | 6/2013 | Talalay | .................. | A23L 29/06 |
| | | | | | 424/94.61 |
| 2014/0227204 | A1 | 8/2014 | Turkowitz | | |
| 2014/0323586 | A1 | 10/2014 | Kinoshita et al. | | |
| 2016/0235057 | A1 | 8/2016 | Qiu et al. | | |
| 2018/0177197 | A1 | 6/2018 | An et al. | | |

FOREIGN PATENT DOCUMENTS

| CN | 105593298 A | 5/2016 |
| EP | 2 623 108 A1 | 8/2013 |
| JP | 2001-064185 A | 3/2001 |
| JP | 2001-199805 A | 7/2001 |
| JP | 2002-363053 A | 12/2002 |
| JP | 2003-155221 A | 5/2003 |
| JP | 2007-161668 A | 6/2007 |
| JP | 2007-169192 A | 7/2007 |
| JP | 2008-079528 A | 4/2008 |
| JP | 2009-114152 A | 5/2009 |
| JP | 2011-500680 A | 1/2011 |
| JP | 2011-519572 A | 7/2011 |
| JP | 2019-202987 A | 11/2019 |
| KR | 10-2017-0114773 A | 10/2017 |
| WO | WO 2009/051739 A1 | 4/2009 |
| WO | WO 2009/135916 A1 | 11/2009 |
| WO | WO 2017/111069 A1 | 6/2017 |

OTHER PUBLICATIONS

Mowad, Christen M. "Allergic contact dermatitis caused by parabens: 2 case reports and a review." American Journal of Contact Dermatitis 11.1 (2000): 53-56. (Year: 2000).*
Jewell, Christopher, et al. "Hydrolysis of a series of parabens by skin microsomes and cytosol from human and minipigs and in whole skin in short-term culture." Toxicology and applied pharmacology 225.2 (2007): 221-228. (Year: 2007).*
Ozaki, Hitomi, et al. "Comparative study of the hydrolytic metabolism of methyl-, ethyl-, propyl-, butyl-, heptyl-and dodecylparaben by microsomes of various rat and human tissues." Xenobiotica 43.12 (2013): 1064-1072. (Year: 2013).*
Oesch, F., et al. "Xenobiotic-metabolizing enzymes in the skin of rat, mouse, pig, guinea pig, man, and in human skin models." Archives of Toxicology 88.12 (2014): 2135-2190. (Year: 2014).*

(Continued)

*Primary Examiner* — Bethany P Barham
*Assistant Examiner* — Peter Anthopolos
(74) *Attorney, Agent, or Firm* — Sterne, Kessler, Goldstein & Fox P.L.L.C.

(57) ABSTRACT

To provide a method for evaluating or selecting an agent for reducing sensory irritation, which reduces sensory irritation caused by parabens, and an agent for reducing sensory irritation, which reduces sensory irritation caused by parabens. A method for evaluating or selecting an agent for reducing sensory irritation caused by parabens, comprising the following steps (1) to (3): (1) a step of contacting cells capable of expressing CES1 with a test substance; (2) a step of measuring expression of CES1 in the cells; (3) a step of evaluating a test substance which promotes expression of CES1 as an agent for reducing sensory irritation caused by parabens based on the results measured in (2).

8 Claims, 6 Drawing Sheets

(56) References Cited

OTHER PUBLICATIONS

Talalay, Paul, et al. "Sulforaphane mobilizes cellular defenses that protect skin against damage by UV radiation." Proceedings of the National Academy of Sciences 104.44 (2007): 17500-17505. (Year: 2007).*
International Search Report (ISR) for PCT/JP2018/043990; I.A. fd Nov. 29, 2018, mailed Feb. 26, 2019, from the Japan Patent Office, Tokyo, Japan.
International Preliminary Report on Patentability (IPRP), Chapter I of the Patent Cooperation Treaty, including the Written Opinion, for PCT/JP2018/043990; I.A. fd Nov. 29, 2018 issued Jun. 2, 2020, by the International Bureau of WIPO, Geneva, Switzerland.
Ninomiya, Rie et al., "Review on usefulness of broccoli sprout extract for sensory stimulation of parabens," J. Japanese Cosmetic Sci. Soc, (Sep. 2018) 42(3):184, (Research IV-R12), Issn 1880-2532.
Maruichi, T et al., "Transcriptional Regulation of Human Carboxylesterase 1A1 by Nuclear Factor-Erythroid 2 Related Factor 2 (Nrf2)," Biochem Pharmacol . Jan. 15, 2010;79(2):288-95. doi: 10.1016/j.bcp.2009.08.019. Epub Aug. 26, 2009.
Chen, YT et al., "Antioxidant Sulforaphane and Sensitizer Trinitrobenzene Sulfonate Induce carboxylesterase-1 Through a Novel Element Transactivated by Nuclear factor-E2 Related factor-2," Biochem Pharmacol . Sep. 15, 2012;84(6):864-71. doi: 10.1016/j.bcp.2012.06.025. Epub Jul. 6, 2012.
Jewell, C et al., "Hydrolysis of a Series of Parabens by Skin Microsomes and Cytosol From Human and Minipigs and in Whole Skin in Short-Term Culture," Toxicol Appl Pharmacol . Dec. 1, 2007;225(2):221-8. doi: 10.1016/j.taap.2007.08.002. Epub Aug. 16, 2007.
Ishiwatari, S et al., "Effects of Methyl Paraben on Skin Keratinocytes," J Appl Toxicol. Jan-Feb. 2007;27(1):1-9. doi: 10.1002/jat.1176.
The extended European Search Report (EESR), including the supplementary European search report and the European search opinion, for European Patent Application No. 18882405.6, dated Jul. 16, 2021, from the European Patent Office, Munich, Germany.
Abbas S, et al., "Metabolism of parabens (4-hydroxybenzoic acid esters) by hepatic esterases and UDP-glucuronosyltransferases in man." Drug Metab Pharmacokinet. 2010;25(6):568-77. doi: 10.2133/dmpk.dmpk-10-rg-013. Epub Oct. 1, 2010. PMID: 20930423.
Ninomiya, Rie et al., (Kao Corporation Safety Science Institute, et al.), "The role of metabolic activity in the skin in the sensory intensity of methylparapen," Japanese Dermatological Association Magazine vol. 128, No. 5, P13(O14-7) on p. 1175, issue date: May 15, 2018; publication date: May 12, 2018.
Hu Lin, "New progress in the treatment of common complications of neuraxial anesthesia," China Foreign Medical Treatment, No. 9, Mar. 21, 2011, pp. 190-192.
Ninomiya R, et al.,. "Sensory irritation to methylparaben is caused by its low metabolism in the skin." J Dermatol. Jul. 2023;50(7):888-894. doi: 10.1111/1346-8138.16775. Epub Mar. 22, 2023.

* cited by examiner

METHOD FOR TREATING SKIN IRRITATION CAUSED BY PARABENS

FIELD OF THE INVENTION

The present invention relates to a method for evaluating or selecting an agent for reducing sensory irritation, which suppresses sensory irritation caused by parabens, and an agent for reducing sensory irritation, which alleviates irritation caused by parabens.

BACKGROUND OF THE INVENTION

An external agent for the skin such as a skin cosmetic is often prepared by blending an antiseptic therein, in order to prevent contamination and propagation of bacteria. Parabens, in particular, is blended the most in an external agent for the skin as an antiseptic having both high antimicrobial activity and high safety. However, those who have a skin sensitive to ultraviolet light, dry conditions and chemical substances, what we call a sensitive skin, may feel a transient, uncomfortable irritation caused by parabens, such as a stinging sensation or a tingling sensation.

To respond to this, a conventional substance suppressing irritation on the skin has been reported, e.g., an agent for suppressing irritation caused by surfactant, which contains a hydrophobic group-containing polysaccharide derivative (Patent Literature 1) and an agent for suppressing irritation for a hair dye, which suppresses irritation caused by a hair dye (Fatent Literature 2). It has been also reported that a TRPA1 inhibitor may be used as an agent for suppressing irritation caused by parabens (Patent Literature 3).

Meanwhile, broccoli sprouts, which are a germinated seeds of broccoli (*Brassies aleracea* var. *italica*) belonging to the family *Brassicaceae*, genus *Brassica*, are known as a plant with a high content of sulforaphane. An extract thereof has been reported to have actions of whitening, and preventing and improving wrinkles and sagging (Patent Literature 4), and have an action of promoting production of sebum (Patent Literature 5). However, there is no report stating that the extract of broccoli sprouts or sulforaphane prevents or improves sensitive skin.

[Patent Literature 1] JP-A-2001-64185
[Patent Literature 2] JP-A-2002-363053
[Patent Literature 3] JP-A-2003-79528
[Patent Literature 4] JP-A-2003-155221
[Patent Literature 5] Japanese Patent Application No. 2009-114152

SUMMARY OF THE INVENTION

The present invention provides the following 1) to 11).

A method for evaluating or selecting an agent for reducing sensory irritation caused by parabens, comprising the following steps (1) to (3):
(1) a step of contacting cells capable of expressing CES1 with a test substance;
(2) a step of measuring expression of CES1 in the cells;
(3) a step of evaluating a test substance which promotes expression of CES1 as an agent for reducing sensory irritation caused by parabens based on the results measured in (2).

2) An agent for reducing sensory irritation, comprising, as an active ingredient, sulforaphane, or a plant or an extract thereof comprising sulforaphane or a glycoside thereof.

3) An agent for promoting expression of CES1, comprising, as an active ingredient, sulforaphane, or a plant or an extract thereof comprising sulforaphane or a glycoside thereof.

4) Use of sulforaphane, or a plant or an extract thereof comprising sulforaphane or a glycoside thereof, for producing an agent for reducing sensory irritation.

5) Use of sulforaphane, or a plant or an extract thereof comprising sulforaphane or a glycoside thereof, for producing an agent for promoting expression of CES1

6) Sulforaphane, or a plant or an extract thereof comprising sulforaphane or a glycoside thereof, for use in reducing sensory irritation.

7) Sulforaphane, or a plant or an extract thereof comprising sulforaphane or a glycoside thereof, for use in promoting expression of CES1.

8) Non-therapeutic use of sulforaphane, or a plant or an extract thereof comprising sulforaphane or a glycoside thereof, for reducing sensory irritation.

9) Non-therapeutic use of sulforaphane, or a plant or an extract thereof comprising sulforaphane or a glycoside thereof, for promoting expression of CES1.

10) A method for reducing sensory irritation, comprising U3ing sulforaphane, or a plant or an extract thereof comprising sulforaphane or a glycoside thereof. 11) A method for promoting expression of CES1, comprising using sulforaphane, or a plant or an extract thereof comprising sulforaphane or a glycoside thereof.

DETAILED DESCRIPTION OF THE EMBODIMENTS

The present invention relates to a provision of a method for evaluating or selecting an agent for reducing sensory irritation, which reduces sensory irritation caused by parabens. The present invention also relates to a provision of an agent for reducing sensory irritation, which reduces sensory irritation caused by parabens.

The present inventors have conducted studies on sensory irritation caused by parabens, and, as a result, have found that methylparaben is metabolized to p-hydroxybenzoic acid (PHBA) by a metabolic enzyme, carboxylesterase 1 (CES1) in a living body, and this PHBA produces little sensory irritation, and that the expression of CES1 in a person with sensitive skin is lower than that in a healthy person, and further found that an agent for reducing sensory irritation caused by parabens can be searched or evaluated by using the expression of CES1 as an indicator. The present inventors also have found that sulforaphane and an extract of a plant containing sulforaphane, such as broccoli sprouts, have an action of promoting the expression of CES1, and they can be an agent for reducing sensory irritation having an effect for reducing sensory irritation caused by parabens.

According to the present invention, an agent for reducing sensory irritation with a novel mechanism, which quickly decomposes parabens in a living body to reduce sensory irritation caused by parabens, can be searched or evaluated.

Furthermore, according to the present invention, an agent for reducing sensory irritation with a novel mechanism, which quickly decomposes parabens in a living body to reduce sensory irritation caused by parabens, ca be provided.

In the present invention, examples of the "paraben" include paraoxybenzoate such as methyl paraben (methyl p-hydroxybenzoate), ethyl paraben (ethyl p-hydroxybenzoate), propyl paraben (propyl p-hydroxybenzoate), isopropyl paraben (isopropyl p-hydroxybenzoate), butyl paraben (butyl p-hydroxybenzoate), isobutyl paraben (isobutyl p-hydroxybenzoate) and benzyl paraben (benzyl p-hydroxybenzoate) and a sodium salt thereof.

Furthermore, "reducing sensory irritation caused by parabens" means suppressing or alleviating a transient uncomfortable irritation on the skin, such as a stinging sensation or a tingling sensation, caused by parabens.

In the present invention, "CES1" refers to carboxylesterase 1, which is also known as serine esterase 1 or SES1. This enzyme is a member of the family of mammalian liver carboxylesterases (EC 3.1.1.1) and hydrolyzes an endogenous substrate having an ester, thioester or amide functional group. CES1 has been reported to be expressed in the lung3 and the skin of humans as well as the liver. The enzyme is involved in metabolic activation of drugs and detoxification of a xenobiotic substance such as chemical substances.

Figure 1:
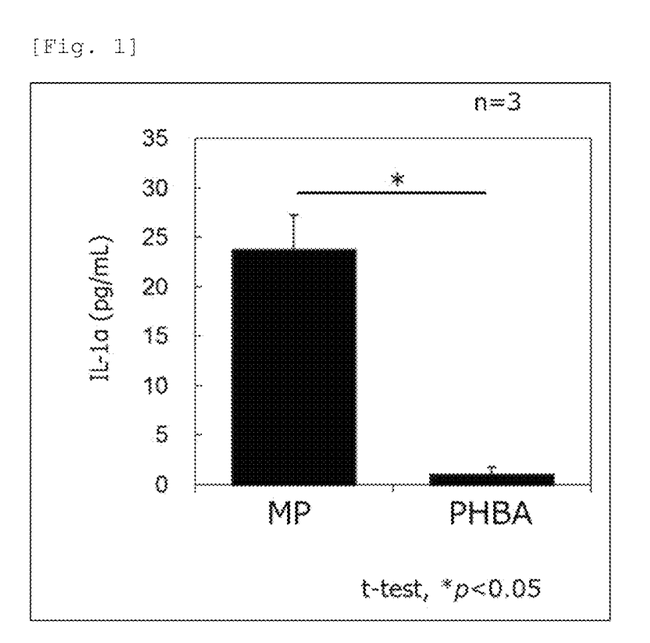
FIG. 1 shows the amount of IL-1α produced in three-dimensional cultured epidermal cells. MP: methyl p-hydroxybenzoate added, PHBA: p-hyaroxybenzoic acid added. Data is shown in a mean value±SD.
Figure 2:
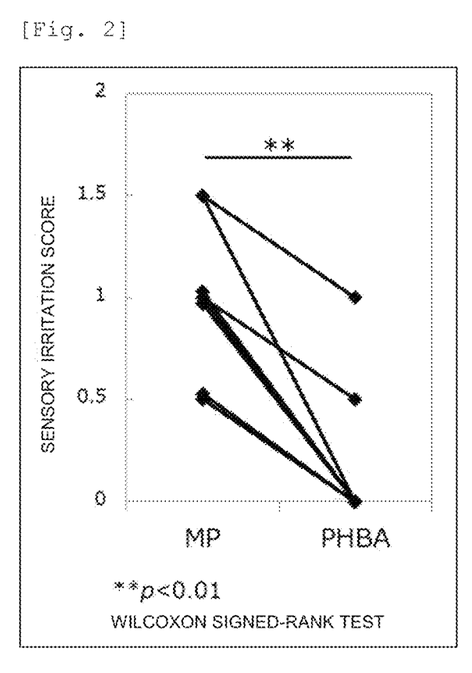
FIG. 2 shows the scores of sensory irritation on the skin of subjects with sensitive skin. MP: methyl p-hydroxybenzoate applied, PHBA: p-hydroxybenzoic acid applied

As shown in Examples described later, when methyl p-hydroxybenzoate (MP) or p-hyaroxybenzoic acid (PHBA) was added to a three-dimensional cultured human epidermis model, the model was cultured, and then the amount of inflammatory cytokine (IL-1α) in the cultured medium was measured, production of IL-1α was increased ir. case of MP addition, but little production of IL-1α was observed in case of PHBA addition(FIG. 1). Furthermore, when MP or PHBA was applied to the skin of those aware of having sensitive skin and irritation was tested, they felt some irritation in case of MP application, while they felt little irritation in case of PHBA application (FIG. 2).

Figure 3:
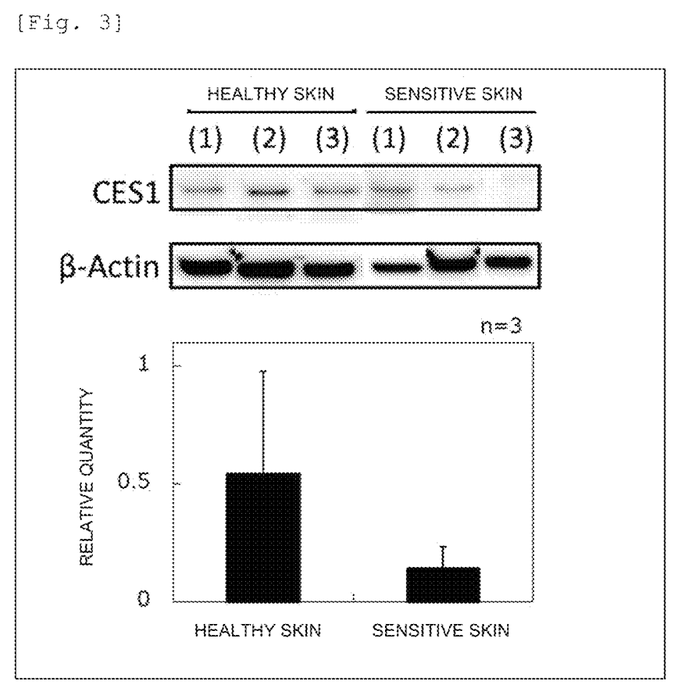
FIG. 3 shows the CES1 expression levels in healthy subjects and subjects with sensitive skin. Data is shown in a mean value±SD.
Figure 4:
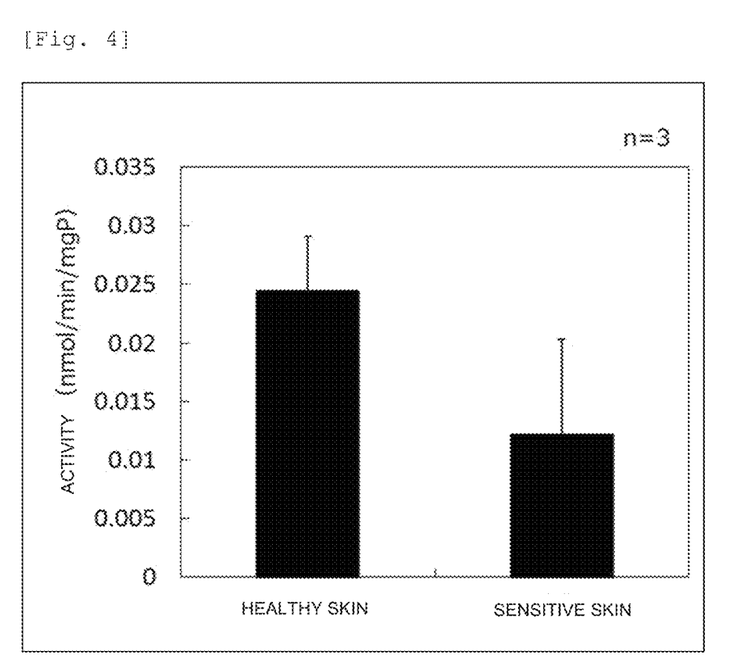
FIG. 4 shows the methyl p-hydroxybenzoate metabolizing activity in healthy subjects and subjects with sensitive skin. Data is shown in a mean value±SD.

Furthermore, when the skin was sampled from healthy subjects and subjects with sensitive skin to measure the MP metabolizing activity and the CES1 expression level in the skin, it was found that the MP metabolizing activity was lower and the CES1 expression level was significantly lower in the skin of the subjects with sensitive skin than those in the skin of the healthy subjects (FIGS. 3 and 4).

These results suggest that a substance which promotes the expression of CES1 are useful as an agent for reducing sensory irritation caused by parabens and that it is possible to evaluate or select an agent for reducing sensory irritation caused by parabens by using the expression of CES1 as an indicator.

The method for evaluating or selecting an agent for reducing sensory irritation caused by parabens includes the following steps (1) to (3):

(1) a step of contacting cells capable of expressing CES1 with a test substance;

(2) a step of measuring expression of CES1 in the cells;

(3) a step of evaluating a test substance which promotes expression of CES1 as an agent for reducing sensory irritation caused by parabens based on the results measured in (2).

In this regard, examples of the "cells capable of expressing CES1" include cells which inherently have CES1 gene and are capable of expressing it and cells into which CES1 gene has been exogenously and expressibly introduced. The cells may be cells sampled from a living body or cells contained in a tissue or an organ sampled from a living body, or may be cultured cells. The cells are preferably cells derived from a mammal, and more preferably cells derived from a human.

Examples of the cells which inherently have CES1 gene and are capable of expressing it include cells derived from various tissues of living bodies. The cells are preferably cells derived from a shin sampled from a mammal (preferably a human) such as cells derived from the epidermal tissue (e.g., epidermal keratinocytes) and cells derived from the dermal tissue (e.g., fibroblasts) as well as a cell culture and organ culture derived from those cells. Cells derived from the epidermal tissue are preferred, and epidermal keratinocytes are more preferred.

The cells into which CES1 gene has been exogenously and expressibly introduced may be prepared by introducing an expression vector containing CES1 gene into any mammalian cells to transform the cells. The transcription regulatory region (e.g., promotors) in the expression vector is not particularly limited as long as the expression can be regulated as in vivo, and it is preferable to use the transcription regulatory region (e.g., promotors) of CES1 gene. As the cells into which CES1 gene has been exogenously and expressibly introduced, cells into which a vector with a reporter gene linked to the transcription regulatory region (e.g., promotors) of CES1 gene is introduced may also be used. Methods of preparing a vector with CES1 gene or the transcription regulatory region (e.g., promotors) of CES1 gene and methods of introducing the vector into mammalian cells are known to those skilled in the art.

Furthermore, examples of the cultured cells include the cells which inherently have CES1 gene and are capable of expressing it and the cultured cells derived from the cells into which CES1 gene have been exogenously and expressibly introduced, as described above as well as cell lines capable of expressing CES1. Cultured cells derived from the skin sampled from a mammal (preferably a human) are preferred, and cultured normal human epidermal keratinocytes are more preferred. Furthermore, three-dimensional cultured skin ceils are preferably used. Specific examples thereof include EpiDerm™ (made by MatTek Corporation), EpiSkin (made by SkinEthic), RHE (made by SkinEthic) and Labcyte EPI-MODEL (made by J-TEC) .

The test substance brought into contact with the above cells is not limited as long as it is intended to be used as an agent for reducing sensory irritation caused by parabens. Examples thereof include an animal, and a plant, a marine organism, a microorganism, an extract thereof; a natural component derived therefrom; a synthetic compound; and a mixture and composition thereof.

Means for contacting the test substance with the above ceils may be means known in this field, and examples thereof include addition of the test substance to a cell culture medium and a direct addition to cells (e.g., dropping, coating, scattering, spraying and patches). The concentration and the amount of the test substance to be brought into contact may be adjusted based on the form, chemical properties, cytotoxicity, and the predicted intensity of skin sensitization of the test substance. For example, a predetermined amount of a test substance which has been diluted to a suitable concentration is exposed to the celis in conditions of 37° C. and 5% $CO_2$ for 24 to 48 hours.

The expression of CES1 in the above cells may be measured using, as an indicator, the expression of CES1 protein, the activity of CES1 protein, the expression of CES1 mRNA encoding the protein and the activation of CES1 gene promoter. The measurement may be carried out by a method known in the art as a method for measuring a parameter used as an indicator (e.g., expression of protein, biological activity of protein, expression of mRNA, activation of CES1 gene promoter).

Examples of the method for measuring the expression of mRNA include dot blotting, Northern blotting, RT-PCR, real-time RT-PCR, microarrays and a combination thereof.

Examples of the method for measuring the activity of CES1 gene promoter include fluorescent/optical measurement of promoter activity or transcription activity using a reporter gene (reporter assays).

Examples of the method for measuring the expression of protein include SDS-PAGE, chromatography, immunological measurement (e.g., immunohistochemical methods, ELISA, Western blotting, immunoprecipitation), colorimetric methods, mass spectrometry, and a combination thereof.

The activity of CES1 protein may be measured by, for example, exposing methyl p-hyaroxybenzoate, which is a substrate of CES1, to cells expressing CES1, culturing the cells for a predetermined time, and then determining the amount of p-hydroxybenzoic acid in the cultured broth by HPLC.

Next, the effect of promoting the expression of CES1 of the test substance is evaluated based on the expression measured as described above. The effect is evaluated by, for example, comparing the results before and after addition of the test substance, or comparing a test substance-addition group and a test substance-free group or a control substance-addition group. Alternatively, the effect may be evaluated by comparing the results of measurement between different concentrations of the test substance.

Then, the test substances which increase or promote the expression of CES1 are selected as an agent for reducing sensory irritation caused by parabens.

The agent for reducing sensory irritation caused by parabens obtained as described above may be blended in a paraben-containing cosmetic, a drug and the like to be used in order to reduce sensory irritation caused by parabens.

According to the above method of the present invention, sulforaphane and an extract of a plant containing sulforaphane such as broccoli sprouts have been found to have the effect of promoting the expression of CES1, and they have been found as an agent for reducing sensory irritation.

Thus, the present invention also provides an agent for reducing sensory irritation or an agent for promoting the expression of CES1, comprising, as an active ingredient, sulforaphane, or a plant or an extract thereof comprising sulforaphane or a glycoside thereof.

As used herein, sulforaphane means 4-(methylsulfinyl) butyl isothiocyanate.

Sulforaphane can be obtained by, for example, isolation and purification from a plant containing sulforaphane or a glycoside thereof by a known method. Sulforaphane isolated and purified is also commercially available from, for example, Sigma-Aldrich. The commercially available product may also be used in the present invention.

In the present invention, not only isolated sulforaphane but also the above plant or the extract thereof containing sulforaphane or a glycoside thereof cany be an active ingredient for the agent for reducing sensory irritation or the agent for promoting the expression of CES1.

Examples of the plant containing sulforaphane or a glycoside thereof include a plant in the family *Brassicaceae*, and preferably a plant in the family *Brassicaceae*, genus *Brassica*. Specific examples thereof include broccoli, cauliflower and cabbage. Of them, in consideration of the content of sulforaphane, broccoli (*Brassica oleracea* var. *itaiica*) is preferred, and broccoli sprouts, sprouted broccoli before maturing, is more preferred.

Examples of a glycoside of sulforaphane include sulforaphane glucosinolate.

As the plant containing sulforaphane or a glycoside thereof, a pulverized product, a lyophilized product or squeezed juice of the whole plant or part of the plant containing sulforaphane or a glycoside thereof can be used. In the case of broccoli sprouts, for example, a dried and pulverized product of part of buds, seed leaves, seeds or roots, or the whole sprouts can be preferably used.

Examples of the extract of the plant include a variety of solvent extraction liquid obtained by extracting the plant by a known method of extraction, a dilution thereof, a concentrate thereof or a dried powde thereof. Examples of the known method of extraction include immersion, exudation, solid-liquid extraction, reflux extraction, supercritical extraction, ultrasonic extraction and microwave extraction. For example, the immersion includes immersion/exudation at 0° C. to the boiling point of the solvent (preferably 15 to 40° C.) for 1 hour to 4 weeks. The solid-liquid extraction includes stirring or shaking at 0° C. to the boiling point of the solvent (preferably 15 to −10° C.) at 30 to 1,000 rpm for 30 minutes to 2 weeks. Furthermore, to prevent oxidation of the extract, means for extraction in a so-called non-oxidizing atmosphere may be used in combination, while dissolved oxygen is removed by boiling deaeration or aeration with inert gas such as nitrogen gas. Furthermore, in reflux extraction, an extractor such as a Soxhlet extractor may be used.

As a solvent for extraction, any of a polar solvent and a non-poiar solvent may be used. Specific examples of the solvent include water; a monohydric, dihydric or polyhydric alcohol; a ketone such as acetone and methyl ethyl ketone; an ester such as methyl acetate and ethyl acetate; a linear or cyclic ether such as diethyl ether and tetrahyarofuran; a polyether such as polyethylene glycol; a saturated or unsaturated hydrocarbon such as hexane; an aromatic hydrocarbon such as benzene and toluene; a halogenated hydrocarbon such as dichloromethane, chloroform, dichloroethane and carbon tetrachloride; a pyridine; dimethyl sulfoxide; acetonitrile; carbon dioxide, supercritical carbon dioxide; fat, wax, other oils; and a mixture thereof. Preferred examples thereof include water, alcohol and a mixture thereof from the viewpoint of the pharmacological activity and applicability.

Examples of the alcohol described above include, but not limited to, a monohydric alcohol such as methanol, ethanol, propanol, butanol, amyl alcohol, hexanol, heptanol and octanol; a dihydric alcohol such as 1,3-butylene glycol, ethylene glycol, propylene glycol, 1,4-butanediol, 1,5-pentanediol and 1,6-hexanediol; and a trihydric or higher alcohol such as glycerol. Of them, a monohydric alcohol and a dihydric alcohol are preferred from the viewpoint of the pharmacological activity and workability. The above alcohol may also be preferably alcohol having 1 to 10 carbon atoms, and more preferably alcohol, having 1 to 4 carbon atoms.

Preferred examples of the alcohol described above include methanol, ethanol, 1,3-butylene glycol, n-propanol, isopropar.ol, n-butanoi, isobutanol, sec-butanol and t-butanol.

The concentration of the above alcohol in an aqueous solution of the alcohol is preferably 20% by mass or more, more preferably 30% by mass or more, and further preferably 40% by mass or more, and preferably 80% by mass or less, more preferably 70% by mass or less, and further preferably 60% by mass or less. The concentration of the above alcohol in an aqueous solution of the alcohol is preferably from 20 to 80% by mass, more preferably from 30 to 70% by mass, and further preferably from 40 to 60% by mass.

Of the above alcohols, ethanol is more preferred from the viewpoint of the applicability. Thus, more preferred examples of the solvent for preparing the extract of a plant described above include water, ethanol and an aqueous solution of ethanol.

It is preferable that the amount of the solvent to be used in extraction is from 1 to 1,000 mL based on 1 g of the plant (in terms of dry mass). As used herein, volume means volume at 25° C. Furthermore, the dry mass means the mass of a dried solid, which is a residue obtained by drying a sample in an electric constant temperature dryer at 105° C. for 3 hours to remove volatile substances. The conditions of extraction are not particularly limited as long as sufficient extraction can be performed. For example, the extraction time is preferably 1 hour or more, more preferably 3 days or more, and further preferably 1 week or more, and preferably 2 months or less, more preferably 5 weeks or less, and further preferably 2 weeks or less. The temperature of extraction is preferably 0° C. or more, and more preferably 5° C. or more, and preferably the boiling point of the solvent or less, and more preferably 90° C. or less. Usually extraction is performed for a longer time at a lower temperature and for a shorter time at a higher temperature. The conditions of extraction include, for example, 15 to 40° C. for 3 days to 5 weeks, preferably 1 to 2 weeks, and 60 to 90° C. for 1 to 5 hours, but are not limited thereto, and may be suitably selected by those skilled in the art.

In the present invention, the plant extract may be directly used, or the extract may be diluted, concentrated or dried and then prepared into powder or paste to be used. Alternatively, the extract may be lyophilized, and when in use, diluted with a solvent usually used for extraction, such as water, ethanol, propylene glycol, 1,3-butylene glycol, a mixture of water and ethanol, a mixture of water and propylene glycol or a mixture of water and 1,3-butylene glycol. The extract may also be included in a vesicle such as liposome, or a microcapsule or the like, and used.

The content of sulforaphane in the plant extract obtained as described above may be increased by subjecting the extract to an isolation and purification step of, for example, treatment using a synthetic adsorbent, filtration treatment and concentration treatment, if necessary. An extract of broccoli sprouts ir. which the content of sulforaphane has been increased, e.g., "Broccoli Sprout Extract," (Oryza Oil & Fat Chemical Co., Ltd.) is commercially available. Such a product may also be used in the present invention.

As shown in Examples described later, sulforaphane and an extract of broccoli sprouts, which is a plant containing sulforaphane, have an action of promoting the expression of CES1 and an action of reducing sensory irritation caused by parabens.

Thus, sulforaphane, or a plant or an extract thereof comprising sulforaphane or a glycoside thereof can be an agent for reducing sensory irritation or an agent for promoting the expression of CES1. Furthermore, they may be used for reducing sensory irritation and promoting the expression of CES1, and may also be used for producing an agent for reducing sensory irritation or an agent for promoting the expression of CES1.

As used herein, "use" means administration to or intake in a human or a non-human animal. Furthermore, the use may be a therapeutic use or non-therapeutic use. The term "non-therapeutic" is a concept which does not include medical practice, i.e., a concept which does not include a method of operation, therapy or diagnosis of a human, more specifically, a concept which does not include a method of operation, therapy or diagnosis of a human by a physician or a person instructed by a physician.

"Reducing sensory irritation" in the "agent for reducing sensory irritation" of the present invention means suppressing or alleviating a transient uncomfortable irritation on the skin, such as a stinging sensation or a tingling sensation, caused by parabens. As used herein, the "paraben" is as described above. The effect of reducing sensory irritation described above can be measured in a sensory evaluation shown in Examples described later.

Furthermore, the "expression of CES1" in the "agent for promoting expression of CES1" includes the expression of CES1 protein, the activity of CES1 protein, the expression of CES1 mRNA encoding the protein and the activity of CES1 gene promoter as described above, and is preferably the expression of CES1 mRNA.

The agent for reducing sensory irritation or the agent for promoting the expression of CES1 may contain sulforaphane, or a plant or an extract thereof containing sulforaphane or a glycoside thereof alone, or may be a composition containing it in combination with an additive or an excipient used for various preparations including a drug, a cosmetic, a quasi drug and a daily product, such as an oil component, a coloring matter, a perfume, an antiseptic, a chelating agent, a pigment, an antioxidant, vitamins, minerals, a sweetener, a seasoning, a preservative, a binder, an extender, a disintegrant, a surfactant, a lubricant, a dispersant, a buffer, a coating agent, a carrier and a diluent. The form of the agent is not particularly limited, and the agent may be prepared in any form of a solution, an emulsion, a suspension, a gel, a solid, a powder, a granule and an aerosol.

The amount of sulforaphane, or a plant or an extract thereof containing sulforaphane or a glycoside thereof to be blended in the composition is 0.0001% by mass or more, preferably 0.001% by mass or more, more preferably 0.01% by mass or more, and further preferably 0.1% by mass or more, and 99% by mass or less, preferably 95% by mass or less, more preferably 90% by mass or less, and further preferably 80% by mass or less, in terms of sulforaphane, based on the total mass of the preparation. The amount is from 0.001 to 99% by mass, preferably from 0.01 to 95% by mass, more preferably from 0.1 to 90% by mass, and further preferably from 1 to 80% by mass. When the composition contains a plant or an extract thereof containing sulforaphane or a glycoside thereof, the content thereof is 0.001% by mass or more, preferably 0.01% by mass or more, more preferably 0.1% by mass or more, and further preferably 1% by mass or more, and 99% by mass or less, preferably 95% by mass or less, more preferably 90% by mass or less, and further preferably 80% by mass or less, in terms of a dry solid, based on the total mass of the preparation. The content is from 0.001 to 99% by mass, preferably from 0.01 to 95% by mass, more preferably from 0.1 to 90% by mass, and further preferably from 1 to 80% by mass.

By blending the agent for reducing sensory irritation or the agent for promoting the expression of CES1 of the present invention into the above paraben-containing composition (e.g., a cosmetic, a quasi drug, a drug and a daily product, such as a skin detergent, a hair detergent, a make-up agent, a bath agent, a preparation for permanent wave, a hair dye, a soap, a kitchen detergent, a laundry detergent and a tooth paste) and using them, or by preparing the agent as a composition different from a paraben-containing composition and using the agent simultaneously with, or before or after using the above paraben-containing composition, irritation caused by parabens can be reduced. In other words, the agent for reducing sensory irritation or the agent for promoting the expression of CES1 of the present invention is applied to preferably a human who uses a paraben-containing composition, and more specifically a human who desires to reduce irritation caused by parabens.

When the agent for reducing sensory irritation or the agent for promoting the expression of CES1 of the present invention is used in combination with a paraben-containing composition, the amount of the agent for reducing sensory irritation or the agent for promoting the expression of CES1 to be used is not particularly limited as long as they reduce sensory irritation. The proportion of sulforaphane, or a plant or an extract thereof containing sulforaphane or a glycoside thereof according to the present invention may be, for example, preferably $10^{-7}$ parts by mass or more, more preferably $10^{-6}$ parts by mass or more, and further preferably $10^{-5}$ parts by mass or more, and preferably 10 parts by mass or less, more preferably 1 part by mass or less, and further preferably 0.1 parts by mass or less, in terms of sulforaphane, based on 1 part by mass of parabens. The proportion may be preferably from $10^{-7}$ to 10 parts by mass, more preferably from $10^{-6}$ to 1 part by mass, and further preferably from $10^{-5}$ to 0.1 part by mass.

For the embodiments described above, the present invention also discloses the following modes.

<1> A method for evaluating or selecting an agent for reducing sensory irritation caused by parabens, comprising the following steps (1) to (3):
(1) a step of contacting cells capable of expressing CES1 with a test substance;
(2) a step of measuring expression of CES1 in the cells;
(3) a step of evaluating a test substance which promotes expression of CES1 as an agent for reducing sensory irritation caused by parabens based on the results measured in (2).

<2> The method according to <1>, wherein the paraben is one or more selected from the group consisting of methylparaben, sodium roethylparaben, ethylparaben, butylparaben, propylparaben, isobutylparaben, isopropylparaben and benzylparaben.

<3> The method according to <2>, wherein the paraben is methylparaben.

<4> The method according to any one of <1> to <3>, wherein the cells capable of expressing CES1 are ceils derived from human epidermal tissue, and preferably cultured normal human epidermal keratinocytes.

<5> The method according to any one of <1> to <4>, wherein the expression of CES1 is measured using, as an indicator, one or more selected from the group consisting of expression of CES1 protein, activity of CES1 protein, expression of CES1 mRNA encoding the protein and activity of CES1 gene promoter, and preferably expression of CES1 mRNA.

<6> An agent for reducing sensory irritation, comprising, as an active ingredient, sulforaphane, or a plant or an extract thereof comprising sulforaphane or a glycoside thereof.

<7> An agent for promoting expression of CES1, comprising, as an active ingredient, sulforaphane, or a plant or an extract thereof comprising sulforaphane or a glycoside thereof.

<8> Use of sulforaphane, or a plant or an extract thereof comprising sulforaphane or a glycoside thereof, for producing an agent for reducing sensory irritation.

<9> Use of sulforaphane, or a plant or an extract thereof comprising sulforaphane or a glycoside thereof, for producing an agent for promoting expression of CES1.

<10> Sulforaphane, or a plant or an extract thereof comprising sulforaphane or a glycoside thereof, for use in reducing sensory irritation.

<11> Sulforaphane, or a plant or an extract thereof comprising sulforaphane or a glycoside thereof, for use in promoting expression of CES1.

<12> Non-therapeutic use of sulforaphane, or a plant or an extract thereof comprising sulforaphane or a glycoside thereof, for reducing sensory irritation.

<13> Non-therapeutic use of sulforaphane, or a plant or an extract thereof comprising sulforaphane or a glycoside thereof, for promoting expression of CES1.

<14> A method for reducing sensory irritation, comprising using sulforaphane, or a plant or an extract thereof comprising sulforaphane or a glycoside thereof.

<15> A method for promoting expression of CES1, comprising using sulforaphane, or a plant or an extract thereof comprising sulforaphane or a glycoside thereof.

<16> The method according to <14> or <15>, wherein the using is using for a human who uses a paraben-containing composition.

<17> In the above <6>, <8>, <10>, <12> or <14>, the sensory irritation is irritation caused by parabens.

<18> In the above <6> to <17>, the plant comprising sulforaphane or a glycoside thereof is broccoli sprouts.

<19> In the above <6> to <18>, the sulforaphane, or the plant or an extract thereof comprising sulforaphane or a glycoside thereof is blended in a paraben-containing composition and used, or is prepared as a composition different from a paraben-containing composition used simultaneously with, or before or after using the above paraben-containing composition.

<20> In the above <19>, the sulforaphane, or the plant or an extract thereof comprising sulforaphane or a glycoside thereof is used in a proportion of preferably $10^{-7}$ parts by mass or more, more preferably $10^{-6}$ parts by mass or more, and further preferably $10^{-5}$ parts by mass or more, and preferably 10 parts by mass or less, more preferably 1 part by mass or less, and further preferably 0.1 parts by mass or less, or in a proportion of preferably from $10^{-7}$ to 10 parts by mass, more preferably from $10^{-6}$ to 1 part by mass, and further preferably from $10^{-5}$ to 0.1 parts by mass, in terms of sulforaphane, based on 1 part by mass of the paraben.

<21> In the above <6> to <9>, the amount of sulforaphane, or the plant or the extract thereof comprising sulforaphane or a glycoside thereof blended in the composition is 0.0001% by mass or more, preferably 0.001% by mass or more, more preferably 0.01% by mass or more, and further preferably 0.1% by mass or more, and 99% by mass or less, preferably 95% by mass or less, more preferably 90% by mass or less, and further preferably 80% by mass or less, or from 0.001 to 99% by mass, preferably from 0.01 to 95% by mass, more preferably from 0.1 to 90% by mass, and further preferably from 1 to 80% by mass, in terms of sulforaphane, based on the total mass of the preparation.

<22> In the above <6> to <9>, the amount of the plant or the extract thereof comprising sulforaphane or a glycoside thereof blended in the composition is 0.001% by mass or more, preferably 0.01% by mass or more, more preferably 0.1% by mass or more, and further preferably 1% by mass or more, and 99% by mass or less, preferably 95% by mass or less, more preferably 90% by mass or less, and further preferably 80% by mass or less, or from 0.001 to 99% by mass, preferably from 0.01 to 95% by mass, more preferably from 0.1 to 90% by mass, and further preferably from 1 to 80% by mass, in terms of a dry solid, based on the total mass of the preparation.

EXAMPLES

Hereinafter, the present invention will be described in more detail with reference to Examples, but the present invention is not limited thereto.

Reference Example 1 Comparison of sensory irritation caused by parabens (Evaluation with three-dimensional cultured epidermis)

LabCyte EPI-MODEL 24 (made by Japan Tissue Engineering Co., Ltd.) was used as a three-dimensional cultured human epidermis model. The culture insert was pre-cultured (5% $CO_2$, 37° C.) in a 500 μL exclusive assay medium overnight, and the culture insert was transferred to a 24-well plate containing a fresh assay medium. 50 μL of a 16.4 mM aqueous solution of methyl p-hydroxybenzoate (MP) or p-hydroxybenzoic acid (PHBA) was added to the epidermal tissue in the culture insert, and the tissue was cultured for 6 hours. Then the culture insert was washed with phosphate buffer 10 times, and transferred to a 24-well plate containing a fresh assay medium, and post-cultured for 18 hours. After the post-culture, the amount of IL-1α in the medium was determined using Human IL-1 alpha/IL-1F1 Quantikine ELISA Kit (R&D Systems) according to the protocol attached. The results are shown in FIG. 1.

FIG. 1 shows that when PHBA was used, the amount of IL-1α whose production is known to be increased due to substances which cause sensory irritation was much smaller than that when MP was used, suggesting that the sensory irritation caused by PHBA was very mild.

Reference Example 2 Comparison of sensory irritation caused by parabens (Evaluation in humans)

Those who met all of the following criteria were selected as subjects with sensitive skin.
1. Age: 20 to 55 years old
2. Sex: female
3. Aware of having sensitive skin
4. Met one or more of the following a and b
   a. Select and use cosmetics considered to be for sensitive skin
   b. Experienced irritation with a stinging or pricking sensation when used a face wash, a skin care product or a make-up base within one year The subjects selected were tested for Stinging test A according to the following method.

After washing face with a make-up remover and a face wash, conditioning was performed in an environment of a temperature of 23° C. and a humidity of 50% for 5 minutes or more. A 2 cm×5 cm piece of nonwoven fabric which was impregnated with 600 μL of a 16.4 mM aqueous solution of methyl p-hydroxybenzoate or p-hydroxybenzoic acid was contacted to the cheek. For sensory irritation that the subjects felt (sore, stinging, pricking, smart, hot, flushed) 30 seconds, 1 minute, 2 minutes, 3 minutes, and 5 minutes after the start of the contact, the subjects submitted scores (0: nothing felt, 0.5: slightly felt or slight discomfort, 1.0: a little discomfort, 1.5: a little to moderate discomfort, 2.0: moderate discomfort, 2.5: moderate to much discomfort, 3.0: much or unbearable discomfort). A value obtained by subtracting, from the highest score of all the scores after 30 seconds to 5 minutes, the highest score in a test performed in the same manner as above except for using distilled water was determined as the sensory irritation score, and the sensory irritation score was statistically analyzed by the Nilcoxon signed-rank test. The results are shown in FIG. 2.

FIG. 2 shows that the sensory irritation caused by PHBA is very mild, suggesting that FHBA contributes little to sensory irritation.

Reference Example 3 Comparison of expression level and metabolic activity of CES1 between healthy skin and sensitive skin (1) Stinging Test B After washing face with a make-up remover and a face wash, conditioning was performed in an environment of a temperature of 23° C. and a humidity of 50% for 5 minutes or more. A 10 $cm^2$ piece of nonwoven fabric which was impregnated with 600 μL of a 16.4 mM aqueous solution of methyl p-hyaroxyber.zoate was contacted to the right cheek. For sensory irritation that the subject felt 30 seconds, 1 minute, 2 minutes and 3 minutes aftex the contact, the subjects submitted scores (0: nothing felt, 0.5: slightly felt, 1.0: a little felt, 2.0: substantially felt, 3.0: so strongly felt that wanting to remove the nonwoven fabric due to strong irritation). The highest score of all the scores after 30 seconds to 3 minutes was determined as the sensory irritation score of the cheek. Next, after the right side of the neck was cleaned with 70% isopropyl alcohol, a 2 cm×2.5 cm piece of nonwoven fabric which was impregnated with 300 μL of a 16.4 mM aqueous solution of methyl p-hydroxybenzoate (MP) was contacted to the site cleaned. For sensory irritation that the subjects felt 30 seconds, 1 minute, 2 minutes and 3 minutes after the start of the contact, the subjects submitted scores (0: nothing felt, 0.5: slightly felt, 1.0: a little felt, 2.0: substantially felt, 3.0: so strongly felt that wanting to remove the nonwoven fabric due to strong irritation), and the highest score of all the scores after 30 seconds to 3 minutes was determined as the sensory irritation score of the neck.

(2) Selection of Subjects

Three were selected as subjects with healthy skin out of those who met all of the following criteria.
Age: 20 to 55 years old
Sex: Female
Aware of not having sensitive skin
Sensory irritation score of both the cheek and the neck of 0 (nothing felt) in Stinging test B Three were selected as a subject with sensitive skin out of those who met all of the following criteria.
Age: 20 to 55 years old
Sex: Female
Aware of having sensitive skin
Sensory irritation score of the cheek of 2 (substantially felt) or more and sensory irritation score of the neck of 0.5 (slightly felt) or more in Stinging test B (3) Skin Biopsy Three subjects were selected from those with healthy skin and those with sensitive skin, respectively, and the skin was collected from the right side of their neck (the site used in the Stinging tests) by using a 4 mm biopsy punch. The skin collected was immediately frozen using liquid nitrogen and stored at −80° C. until analyzed.

(4) Expression level and activity of carboxylesterase 1 in skin biopsy

A skin biopsy 4 mm in diameter was halved with a knife, and one of the pieces was used for analyzing the expression level of carboxylesterase 1 and the other was used for analyzing the activity of carboxylesterase 1.

The skin biopsy tissue for analyzing the expression level was cut into srips with a scissors. RIPA buffer (Wako Pure Chemical Industries, Ltd.) to which Protease Inhibitor Mixture (Wako Pure Chemical Industries, Ltd.) had been added was added in an amount ((The weight of the tissue (mg)× 20) µL) to a microtube containing the skin biopsy tissue. The mixture was homogenized with a homogenizer (physcotron, MICROTEC CO., LTD.) and then allowed to stand on ice for 30 minutes. After 30 minutes, the mixture was treated with ultrasonic wavs at 4° C. for 2 mintues and centrilfuged at 10,000 rpm at 4° C, for 20 minutes to obtain a supernatant thereof as a skin extract solution. The amount of protein in the skin extract solution was determined using Pierce BCA Protein Assay Kit (Thermo Scientific) with bovine serum albumin as a standard protein.

The sample skin extract solution was subjected to polyacrylamide gel electophoresus (SDS-PAGE) and Western blotting as follows.

After the skin extract solution was separated by SDS-PAGE, the protein was transferred to a PVDF membrane (BIO-RAD). The PVDF membrane after transfer was immersed in a 5% skim milk solution to perform blocking, and then primary antibody reaction was performed using anti-carboxylesterase 1 antibody (R&D Systems, Cat#MAB4920) which had been diluted at 1:200. Secondary antibody reaction was performed using horseradish peroxidase (HRP)-labeled anti-mouse IgG antibody (R&D Systems, Cat#HAF007) which had been diluted at 1:2,000. Luminescence was obtained using Clarity Western ECL Substrate (BIO-RAD), and the antibody reaction was detected using LAS-4000 (FUJIFILM Corporation). The band of CES1 and the band of actin in the image of the Western blotting taken were individually selected by using an image analysis software, CS Analyzer (ATTO Corporation), and the intensity of the bands was measured to calculate the intensity of CES1 based on actin. Whether a constant amount of the samples was loaded into the polyacrylamide gel or not was examined by a test performed in the same manner except for using anti-β-actin antibody as primary antibody.

The skin biopsy tissue for analyzing activity was cut into strips with a scissors. Then, a 50 mM HEPES/150 mM KCl (pH 7.4) solution was added thereto in an amount ((the weight of the tissue (mg)×20) µL), and the mixture was homogenized with a homogenizer (Physcotron, MICROTEC CO., LTD.), and then centrifuged at 10,000 rpm at 4° C. for 20 minutes to obtain a supernatant as a skin extract solution. The amount of protein in the skin extract solution was determined using Pierce BCA Protein Assay Kit (Thermo Scientific). The final concentration of protein in the respective skin extract solutions was adjusted to 50 µg/mL, and methyl p-hydroxybenzoate, which is a substrate of carboxylesterase 1, was added thereto so that the concentration was 200 µM, and the reaction was performed at 37° C. for 5 hours. Then cold acetonitrile was added in the same amount as that of the reaction solution to the reaction solution to stop the reaction. The amount of the metabolite, p-hydroxybenzoic acid, was determined by HPLC, and the amount of p-hydroxybenzoic acid produced per unit protein and unit time was determined as the metabolic activity of CES1. The instrument, column and conditions of measurement used in HPLC are shown below.

Instrument: Alliance 2695 Separation Module, 2996 Photodiode Array Detector (Waters)
Column: L-column ODS (4.6×350 mm, 5 µm, Chemicals Evaluation and Research Institute, Japan)
Column temperature: 40° C.
Mobile phase: 45% methanol/0.1% formic acid
Flow rate: 1.0 mL/minute
Amount of sample injected: 50 µL
Detection wavelength: 254 nm
The results are shown in FIG. 3 and FIG. 4.

FIG. 3 and FIG. 4 show that the expression level of CES1 and the metabolic activity of CES1 were lower in the skin of the subjects with sensitive skin than those in the skin of the subjects with healthy skin.

Example 1 Evaluation of extract of broccoli sprouts based on expression of CES1

Normal human epidermal keratinocytes (Life Technologies Japan Ltd.) were seeded into a 6-well plate so that the number of cells in each well was $1 \times 10^{-5}$, and cultured in HuMedia-KG2 (KURABO INDUSTRIES LTD.) overnight. Then, an extract of broccoli sprouts (Broccoli Sprout Extract, Oryza Oil (. Fat Chemical Co., Ltd., for cosmetics) was added to the culture medium at a solid concentration of 0.0001 w/v % or 0.001 w/v %, and the cells were cultured for 48 hours. The ceils after culture was washed with D-PB3 (−) and RNA was extracted using RNeasy Mini Kits (QIAGEN) according to the manual attached. The RNA concentration was calculated by using NanoDrop 1000 (Thermo Fisher Scientific). Total RNA extracted was reverse-transcribed using High-Capacity RNA-to-cDNA Kit (Life Technologies Japan Ltd.), and then real-time PCR was performed using 7500 Fast Real-Time PCR System (Life Technologies Japan Ltd.). In the real-time PCR, the expression levels of CES1 mRNA were compared by the ΔΔ CT method using the above reverse transcribed cDNA and CES1, or, as an endogenous control, Tsqman primer for RPLP0 (Life Technologies Japan Ltd., CES1:Hs00275627-m1, RPLP0: HS00420695_gH), Taqma.n Gene Expression Master Mix (Life Technologies Japan Ltd.). The results are shown in FIG. 5.

Figure 5:
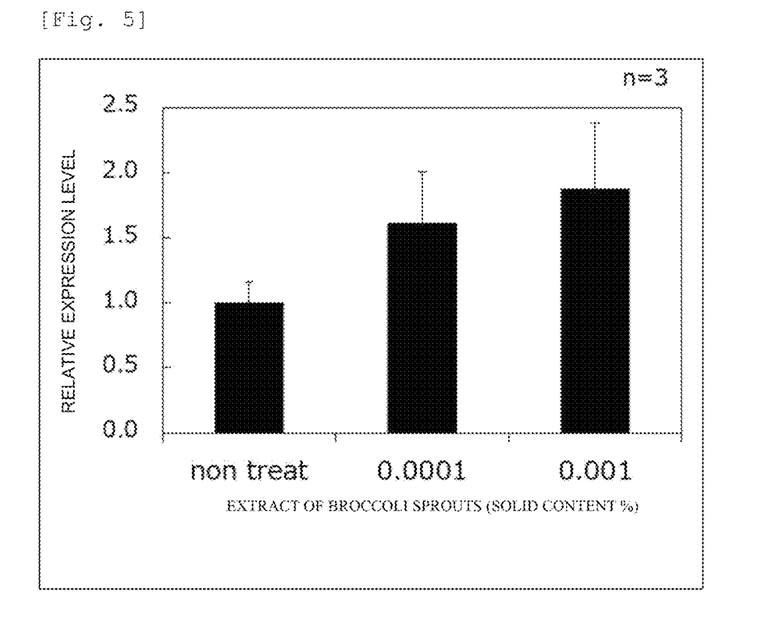
FIG. 5 shows an action of an extract of broccoli sprouts to promote the expression of CES1.

FIG. 5 shows that the extract of broccoli sprouts increased the expression level of CES1 mRNA.

Example 2 Efficacy study of extract of broccoli sprouts for humans

Figure 6:
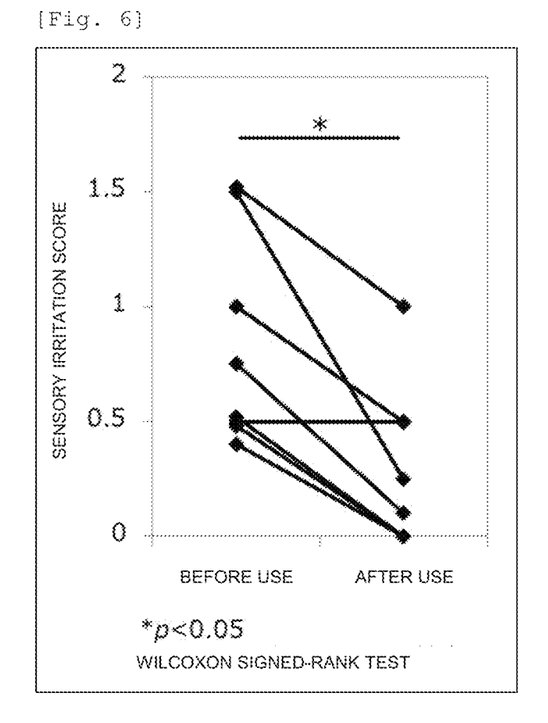
FIG. 6 shows an action of an extract of broccoli sprouts to reduce sensory irritation caused by methyl p-hydroxybenzoate.

Males aware of having a sensitive skin and feeling sensory irritation for methyl p-hydroxybenzoate (MP) were selected as subjects. A 500-yen coin size amount of a 10% ethanol solution containing an extract of broccoli sprouts (Broccoli Sprout Extract, Oryza Oil S Fat Chemical Co., Ltd. for cosmetics) having a solid concentration of 0.01% was applied to the entire face of the subject twice a day for a week, and sensory irritation scores before and after application in Stinging test C were compared. Stinging test C was performed according to the following method.

After washing face with a make-up remover and a face wash, conditioning was performed in an environment of a temperature of 23° C. and a humidity of 50% for 5 minutes or more. A 10 cm² piece of nonwoven fabric which was impregnated with 600 µL of a 16.4 mM aqueous solution of methyl p-hydroxybenzoate was contacted to the cheek. For sensory irritation that the subject felt 30 seconds to 3 minutes after the contact, the subject submitted scores (0: nothing felt, 0.5: slightly felt, 1.0: a little felt, 2.0: substantially felt, 3.0: so strongly felt that wanting to remove the nonwoven fabric due to strong irritation) A value obtained by subtracting, from the highest score of the submitted scores, the highest score in a test performed in the same manner except for using distilled water was determined as the sensory irritation score, and the sensory irritation score was statistically analyzed by the Wilcoxon signed-rank test. The results are shown in FIG. 6.

FIG. 6 shows that the extract of broccoli sprouts reduces sensory irritation caused by methyl p-hydroxybenzoate.

Example 3 Action of suiforaphane to promote expression of CES1

Normal human epidermal keratinocytes (Life Technologies Japan Ltd.) were seeded into a 6-well plate so that the number of cells in each well was $1 \times 10^{-5}$ and cultured in HuMedia-KG2 (KURABO INDUSTRIES LTD.) overnight. Then, suiforaphane (Sigma-Aldrich) was exposed to the cells so that the final concentration was 0.1, 1, and 10 μM, and the cells were cultured for 48 hours. The cells after culture was washed with a phosphate buffer (D-PBS (−)) and RNA was extracted using RNeasy Mini Kits (QIAGEN) according to the manual attached. The RNA concentration was calculated by using NanoDrop 1000 (Thermo Fisher Scientific). Total RNA extracted was reverse-transcribed using High-Capacity RNA-to-cDNA Kit (Life Technologies Japan Ltd.), and then real-time PCR was performed using 7500 Fast Real-Time PCR System (Life Technologies Japan Ltd.). In the real-time PCR, the expression levels of the gene were compared by the ΔΔ CT method using the above reverse transcribed cDNA and carboxylesterase 1, or, as an endogenous control, Taqman primer for RPLP0 (Life Technologies Japan Ltd., CES1:Hs00275627-m1, RPLP0: HS00420895_gH), Taqman Gene Expression Master Mix (Life Technologies Japan Ltd.). The results are shown in Table 1.

TABLE 1

| | Mean value ± SD n = 3 | | |
|---|---|---|---|
| Sulforaphane (μM) | 0.1 | 1 | 10 |
| Relative gene expression level (with non treat as 1.0) | 1.5 ± 0.33 | 3.6 ± 0.90 | 35 ± 8.4 |

Table 1 shows that sulforaphane increased the expression level of CES1 mRNA.

The invention claimed is:

1. A method for treating skin irritation caused by a paraben, the method comprising topically administering to a human in need thereof (i) an effective amount of sulforaphane, or (ii) a plant or an extract thereof comprising an effective amount of sulforaphane or a glycoside thereof.

2. The method of claim 1, wherein the plant is broccoli sprouts.

3. The method of claim 1, wherein the sulforaphane, or the plant or an extract thereof comprising sulforaphane or a glycoside thereof, is blended in a paraben-containing composition.

4. The method of claim 1, wherein the sulforaphane, or the plant or an extract thereof comprising sulforaphane or a glycoside thereof, is blended in a composition that does not contain a paraben.

5. The method of claim 1, wherein the skin irritation is a stinging sensation.

6. The method of claim 1, wherein the skin irritation is a tingling sensation.

7. The method of claim 1, wherein the paraben is methyl p-hydroxybenzoate.

8. The method of claim 1, wherein the paraben is at least one selected from the group consisting of methylparaben, methyl p-hydroxybenzoate, ethylparaben, ethyl p-hydroxybenzoate, propylparaben, propyl p-hydroxybenzoate, isopropylparaben, isopropyl p-hydroxybenzoate, butylparaben, butyl p-hydroxybenzoate, isobutylparaben, isobutyl p-hydroxybenzoate, benzylparaben, benzyl p-hydroxybenzoate, and a sodium salt thereof.

\* \* \* \* \*